US008845671B2

(12) United States Patent
Stien et al.

(10) Patent No.: US 8,845,671 B2
(45) Date of Patent: Sep. 30, 2014

(54) METHOD FOR INSERTING AN IV CATHETER

(75) Inventors: Karl Stien, Eau Claire, WI (US); Nathaniel J. Stewart, Eau Claire, WI (US)

(73) Assignee: Stewart and Stien Enterprises, LLC, Eau Claire, WI (US)

( * ) Notice: Subject to any disclaimer, the term of this patent is extended or adjusted under 35 U.S.C. 154(b) by 220 days.

(21) Appl. No.: 13/425,565

(22) Filed: Mar. 21, 2012

(65) Prior Publication Data

US 2013/0253562 A1 Sep. 26, 2013

(51) Int. Cl.
*A61B 17/00* (2006.01)

(52) U.S. Cl.
USPC ...................................... 606/190; 604/164.1

(58) Field of Classification Search
CPC ........... A61B 17/3421; A61B 17/3403; A61B 17/3415; A61B 17/3417; A61M 25/0606; A61M 29/00
USPC ............... 606/191–199, 185, 190; 604/164.1, 604/170.03, 506, 539
See application file for complete search history.

(56) References Cited

U.S. PATENT DOCUMENTS

| | | | | |
|---|---|---|---|---|
| 3,347,232 A | * | 10/1967 | Ginsburg | ....................... 604/158 |
| 4,239,042 A | | 12/1980 | Asai | |
| 4,543,092 A | | 9/1985 | Mehler et al. | |
| 4,565,545 A | * | 1/1986 | Suzuki | ..................... 604/164.06 |
| 4,581,019 A | | 4/1986 | Curelaru et al. | |
| 4,588,398 A | * | 5/1986 | Daugherty et al. | ............ 604/265 |
| 4,629,450 A | * | 12/1986 | Suzuki et al. | ............... 604/164.1 |
| 4,767,407 A | * | 8/1988 | Foran | ........................ 604/164.06 |
| 4,795,426 A | | 1/1989 | Jones | |
| 5,242,410 A | * | 9/1993 | Melker | ....................... 604/164.1 |
| 5,380,290 A | * | 1/1995 | Makower et al. | ......... 604/164.01 |
| 5,520,657 A | | 5/1996 | Sellers et al. | |
| 5,618,272 A | * | 4/1997 | Nomura | .................... 604/166.01 |
| 5,743,882 A | | 4/1998 | Luther | |
| 5,843,046 A | * | 12/1998 | Motisi et al. | ................... 604/256 |
| 5,944,695 A | | 8/1999 | Johnson et al. | |
| 6,015,401 A | * | 1/2000 | Brackett et al. | ............... 604/506 |
| 6,607,511 B2 | * | 8/2003 | Halseth et al. | ........... 604/164.08 |
| 7,144,386 B2 | | 12/2006 | Korkor et al. | |
| 2006/0178635 A1 | | 8/2006 | Callaway | |
| 2009/0209912 A1 | * | 8/2009 | Keyser et al. | ............... 604/164.1 |

* cited by examiner

*Primary Examiner* — Katrina Stransky

(74) *Attorney, Agent, or Firm* — Wood, Phillips, Katz, Clark & Mortimer

(57) ABSTRACT

A method and apparatus for preparing an access site on a patient for insertion of a catheter into one of the patient's veins. The method includes the steps of: providing a tract forming assembly having a leading cutting edge and a dilating body defining a trailing dilating portion, with the cutting edge and dilating body together defining a tract forming unit; advancing the tract forming unit into skin at the access site so that: a) the cutting edge progressively forms a tract through the patient's skin and subcutaneous tissue towards the one vein; and b) the dilating body follows the cutting edge and dilates the tract; and removing the tract forming unit from the dilated tract so that no component resides in the dilated tract to allow a catheter to be directed through the dilated tract and into the one vein.

24 Claims, 3 Drawing Sheets

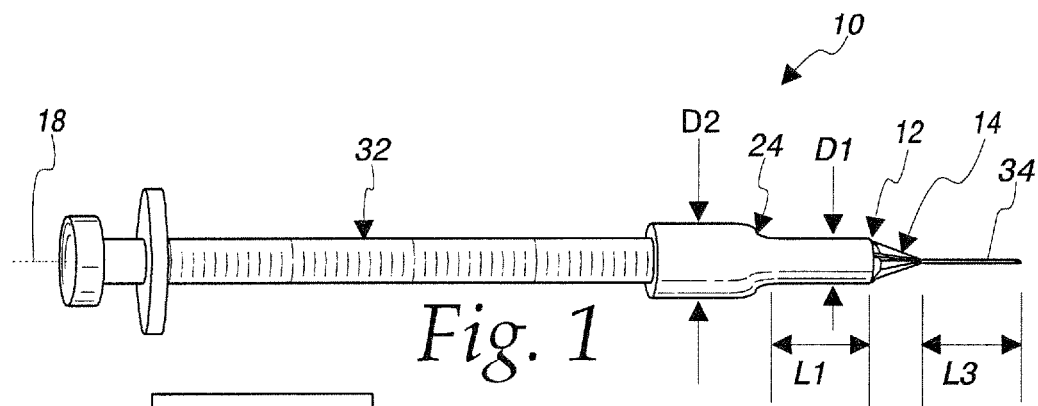
Fig. 1
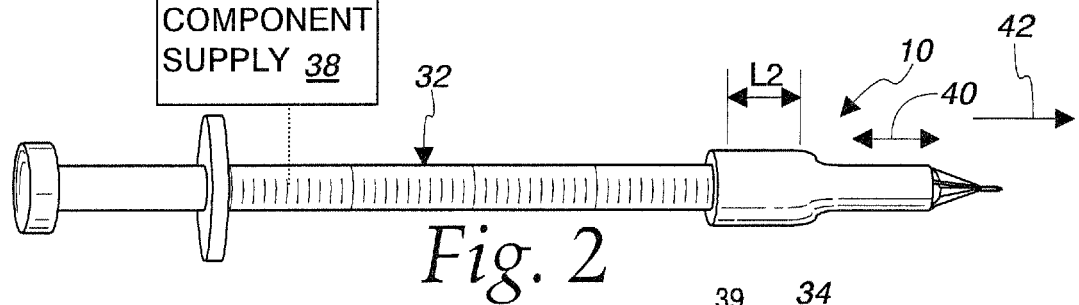
Fig. 2
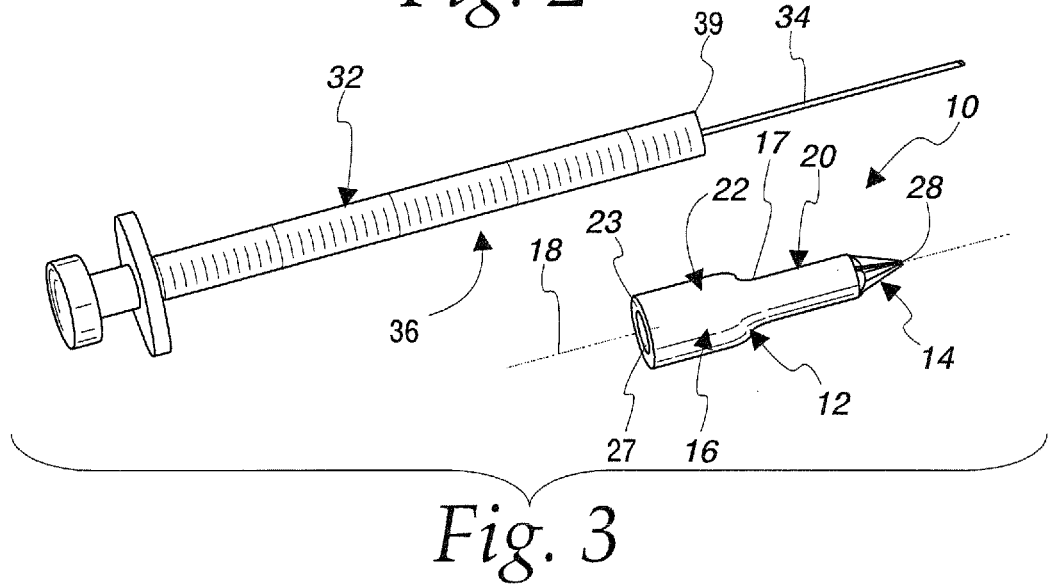
Fig. 3
Fig. 10
Fig. 9

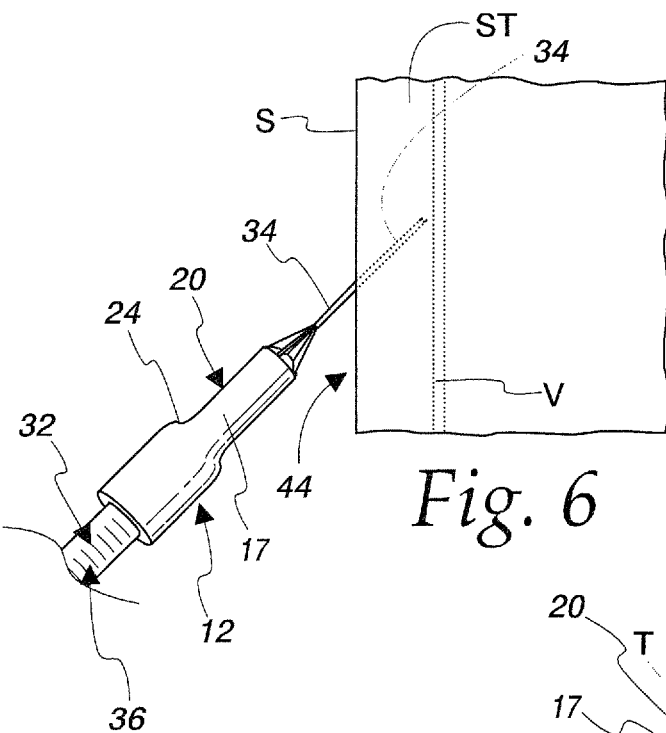
Fig. 6
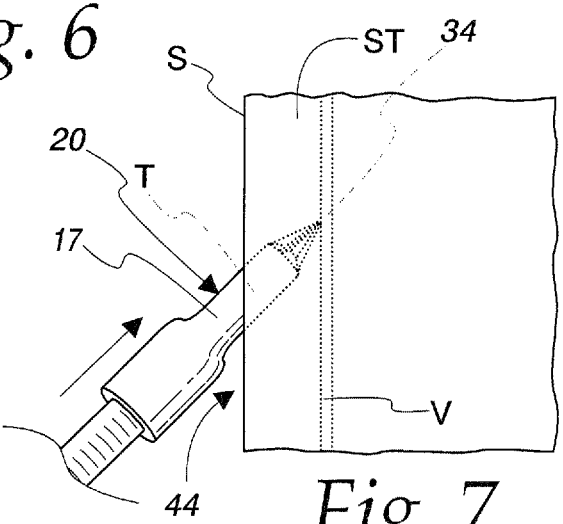
Fig. 7
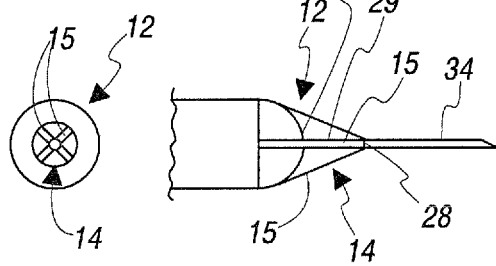
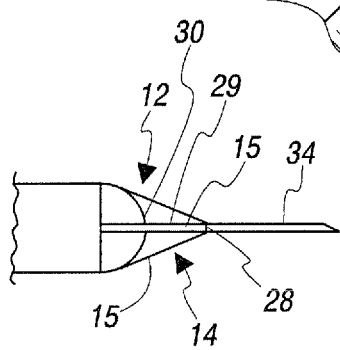
Fig. 4        Fig. 5
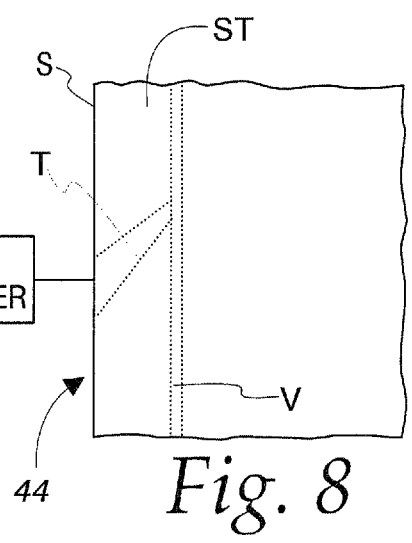
Fig. 8

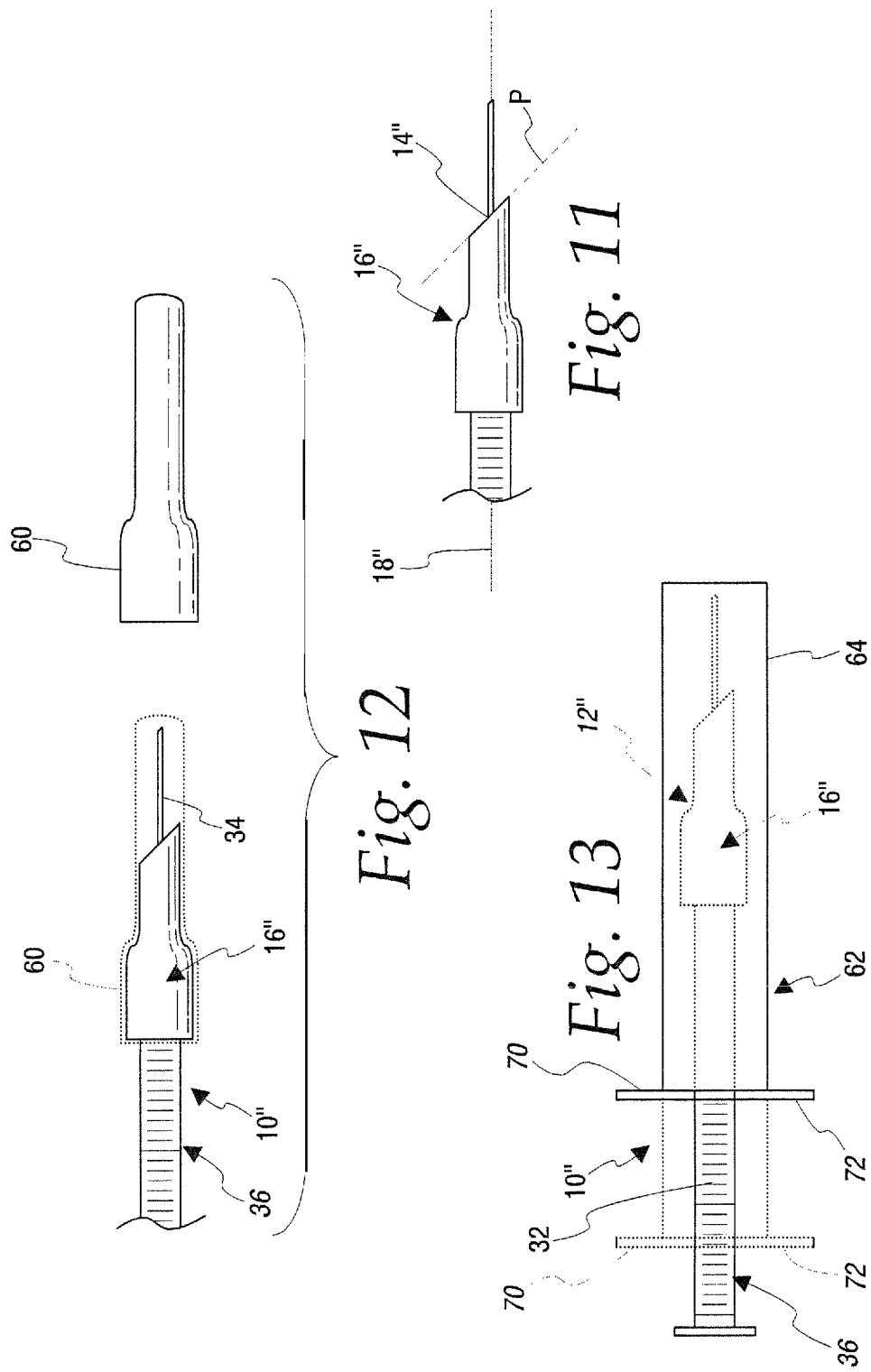

METHOD FOR INSERTING AN IV CATHETER

BACKGROUND OF THE INVENTION

1. Field of the Invention

This invention relates to IV catheters and, more particularly, to a method and apparatus for preparing a site for the insertion of an IV catheter into a vein.

2. Background Art

Many different medical procedures require the insertion and use of an IV catheter. Commonly, a guide cannula is initially directed into a vein. With the cannula within the vein, one or more components can be guided, together or sequentially, along the cannula to enlarge the access opening to the diameter required for the catheter. Some or all of these components remain in place as the catheter is inserted. Many different systems of this type have been devised and are currently used to insert IV catheters. However, these systems generally have some inherent drawbacks.

First of all, the formation of a relatively large tract to accommodate a catheter may cause patient discomfort. In the absence of carrying out a separate local anesthetizing step, patients may experience a significant amount of discomfort as the components are inserted.

These systems also tend to become quite complicated, with some of them requiring the serial use of three or more components to ultimately effect the IV catheter insertion.

These prior art systems may be particularly deficient when it comes to use on patients with medical conditions where the tissue at the insertion site is thickened and/or hardened. With thick tawny skin and/or edematous subcutaneous tissue, it is difficult to control by feel the direction of the IV catheter, and the components inserted preparatory to the insertion of the IV catheter, to the vein location. This problem becomes particularly pronounced since this type of patient also generally has small veins which are barely visible. Consequently, successful IV catheter insertion relies primarily upon feel as opposed to vision. This may result in extended time periods for each attempt and failed attempts to access a vein and/or tissue manipulation during penetration that is painful for a patient. This problem is aggravated by the rigidity of the dermal and/or sub-dermal tissues which produces tension and resistance to the IV catheter and components inserted preparatory to the insertion of the IV catheter. This condition markedly limits the sensitivity necessary to access a vein.

Some patient conditions are so extreme that the IV catheter cannot be feasibly directed into a vein. If a peripheral IV cannot be obtained and IV access is required, it may become necessary to use a PICC line or other central venous catheters which involves components that are more costly and a process that is more time consuming and costly to carry out.

Notwithstanding the limitations of the prior art systems, and the multitude of IV catheter insertions that take place on a regular basis, the medical industry has contended with the above problems. The willingness to contend with these problems is the result of the lack of any viable alternative systems that would address the shortcomings of the prior art.

Designers in the medical field continue to seek systems of this type that allow efficient, pain-free, and precise insertion of IV catheters into veins, regardless of a patient's condition.

SUMMARY OF THE INVENTION

In one form, the invention is directed to a method for preparing an access site on a patient for insertion of a catheter into one of the patient's veins. The method includes the steps of: providing a tract forming assembly with a leading cutting edge and a dilating body defining a trailing dilating portion, the cutting edge and dilating body together defining a tract forming unit; advancing the tract forming unit into skin at the access site so that: a) the cutting edge progressively forms a tract through the patient's skin and subcutaneous tissue towards the one vein; and b) the dilating body follows the cutting edge and dilates the tract; and removing the tract forming unit from the dilated tract to allow a catheter to be directed through the dilated tract and into the one vein.

In one form, the step of advancing the tract forming unit involves advancing the tract forming unit so that the cutting edge forms a tract fully up to the one vein.

In one form, the step of advancing the tract forming unit involves advancing the tract forming unit so that the dilating body dilates the tract fully up to the one vein.

In one form, the step of providing a tract forming assembly involves providing a tract forming assembly wherein the cutting edge moves as one piece with the dilating body.

In one form, the step of providing a tract forming assembly involves providing a tract forming assembly wherein the cutting edge is formed on the dilating body.

In one form, the step of providing a tract forming assembly involves providing a tract forming assembly wherein the dilating body has an axis and leading and trailing ends spaced lengthwise of the dilating body along the axis. The dilating body has a first section with a first axial length with one of: a) a substantially constant diameter; and b) a diameter that increases axially from the leading end towards the trailing end of the dilating body.

In one form, the step of providing a tract forming assembly involves providing a tract forming assembly wherein the dilating body has a second section with a diameter greater than an average diameter of the first section. A transition region is located between the first and second sections.

In one form, the step of providing a tract forming assembly involves providing a tract forming assembly wherein the first and second sections and transition region are formed as one piece.

In one form, the step of providing a tract forming assembly involves providing a tract forming assembly wherein the first section has at least a portion with a diameter on the order of 16 gauge.

In one form, the step of providing a tract forming assembly involves providing a tract forming assembly that additionally includes a cannula with a length. The method further includes the step of advancing the cannula through the patient's skin at the access site. The step of advancing the tract forming unit involves advancing the tract forming unit one of: a) lengthwise along the cannula after the cannula is advanced through the patient's skin; and b) together with the cannula with the tract forming unit and cannula in fixed relationship.

In one form, the step of providing a tract forming assembly involves providing a tract forming assembly that additionally includes a syringe with an anesthetizing component. The method further includes the step of injecting the anesthetizing component in the syringe through the cannula and into the patient at the access site before advancing the tract forming unit into the patient's skin.

In one form, the step of providing a tract forming assembly involves providing a tract forming assembly wherein the cannula extends into and from the tract forming unit. The step of advancing the tract forming unit involves advancing the tract forming unit guidingly over and relative to the cannula.

In one form, the step of providing a tract forming assembly involves providing a tract forming assembly wherein a portion of the syringe is inserted into the tract forming unit.

In one form, the step of providing a tract forming assembly involves providing a tract forming assembly wherein the tract forming unit has an axis. The cutting edge at least one of: a) resides in a plane that is at an angle to the axis; and b) has a plurality of discrete cutting edge portions.

In one form, the invention is further directed to a tract forming assembly for preparing an access site on a patient for insertion of a catheter into one of the patient's veins. The tract forming assembly has a tract forming unit with a leading cutting edge and a dilating body defining a trailing dilating portion. The dilating body has an axis and a length along the axis between leading and trailing ends. The tract forming assembly further has a syringe with a cannula, together defining an injection/guide unit. The cutting edge and dilating body are movable together as one piece. The dilating body has a first section with a length between the cutting edge and the trailing end of the dilating body. The first section has at least a portion with one of: a) a substantially constant diameter; and b) a diameter that increases axially from the leading end towards the trailing end of the dilating body.

In one form, the tract forming unit and injection/guide unit are configured to cooperate so that: a) with the tract forming unit and injection/guide unit in a first state, the cannula projects from the tract forming unit and can be advanced through a patient's skin at an access site towards a vein; and b) with the tract forming unit and injection/guide unit in the first state and the cannula advanced through a patient's skin, the tract forming unit can be advanced guidingly over and relative to the cannula to cause the tract forming unit and injection/guide unit to be changed to a second state, as an incident of which a tract is cut at the access site and thereafter dilated.

In one form, the cutting edge is formed on the dilating body and the dilating body has a second section with a length and a diameter greater than an average diameter of the first section and there is a transition region between the first and second sections. The first and second sections, transition region, and cutting edge are formed as one piece.

In one form, the first section has at least a portion with a diameter on the order of 16 gauge.

In one form, the tract forming unit has a through opening and the injection/guide unit extends into and through the through opening.

In one form, the syringe contains a supply of an anesthetizing component that can be injected at the access site.

In one form, the cutting edge at least one of: a) resides in a plane that is at an angle to the axis of the tract forming unit; and b) has a plurality of discrete cutting edge portions.

In one form, the tract forming assembly is provided in combination with a catheter having a diameter less than the diameter of the portion of the first section.

In one form, the tract forming assembly further includes a cover assembly that can be changed between: a) an operative state, wherein the cutting edge and/or the cannula is exposed; and b) a covering state.

In one form, the cover assembly is connected to at least one of the tract forming and injection/guide unit with the cover assembly in both the operative and covering states.

BRIEF DESCRIPTION OF THE DRAWINGS

FIG. 1 is an elevation view of a tract forming assembly, according to the present invention, and including cooperating tract forming and injection/guide units, with these components in a first state;

FIG. 2 is a view as in FIG. 1 with the tract forming and injection/guide units in a second state;

FIG. 3 is an exploded, perspective view of the tract forming and injection/guide units in FIGS. 1 and 2;

FIG. 4 is an end elevation view of the tract forming unit in FIGS. 1-3;

FIG. 5 is a fragmentary, side elevation view of the leading portion of the tract forming unit and a cannula on the injection/guide unit;

FIGS. 6-8 are sequential views showing the formation of a dilated tract at an access site on a patient utilizing the tract forming assembly in FIGS. 1-5;

FIG. 9 is a schematic representation of a tract forming assembly according to the invention;

FIG. 10 is a schematic representation of a method for preparing an access site on a patient for insertion of a catheter according to the invention;

FIG. 11 is a fragmentary, elevation view of a leading portion of the injection/guide unit with a modified form of tract forming unit according to the invention operatively connected;

FIG. 12 is a fragmentary, side elevation view of the tract forming assembly in FIG. 11 and with an optional cover shown operatively positioned in dotted lines and separated in solid lines; and FIG. 13 is a side elevation view of the tract forming assembly of FIGS. 11 and 12 incorporating a cover assembly, with the cover assembly shown in two different states in solid and dotted lines.

DETAILED DESCRIPTION OF THE PREFERRED EMBODIMENT

In FIGS. 1-5, a tract forming assembly, according to the present invention, is shown at 10. The tract forming assembly 10 consists of a tract forming unit at 12 having a leading cutting edge 14, made up of a plurality of cutting edge portions 15, and a dilating body 16 with a trailing dilating portion 17. The tract forming unit 12 and dilating body 16 each has an axis 18 and a length along the axis 18.

The dilating body 16 has first and second sections 20, 22, respectively, spaced lengthwise of each other. The first section 20 resides between the cutting edge 14 and the second section 22.

The first section 20 has at least a portion thereof with a first diameter D1. At least a portion of the second section 22 has a second diameter D2 that is greater than the first diameter D1.

In the embodiment depicted, the first section 20 has a substantially uniform diameter over its entire length L1, with the second section 22 having a substantially uniform diameter over its entire length L2. It is not a requirement that the diameters be uniform over the respective lengths of the sections 20, 22. In one preferred form, the diameter D1 increases progressively over its length towards a trailing end 23 of the dilating body 16. The diameter D2 is greater than an average diameter of the first section 20.

The dilating body 16 has a transition region at 24 between the first and second sections 20, 22. The transition region 24 curves gradually to blend into the separate sections 20, 22.

The dilating body 16 has a hollow construction defining a through opening 27 between a leading end 28 and the trailing end 23 thereof.

The cutting edge portions 15 on the cutting edge 14 are each defined on a flat blade 29 that increases in radial dimension moving in a trailing direction. A convex surface 30 is formed between the blades 29.

In the depicted embodiment, the first and second sections 20, 22, transition region 24, and cutting edge 14 are all formed as one piece.

While preferred, this is not a requirement. These components could be separately formed but are preferably constructed to at least move together as one piece during the formation of a tract, as described hereinbelow.

The tract forming assembly 10 further includes a syringe 32, with a cannula 34. The syringe 32 and cannula 34 together define an injection/guide unit at 36. The syringe 32 may be, for example, a tb syringe or a 1 cc diabetic or insulin syringe. Other syringe types are contemplated. In one form, the syringe 32 contains an injectable component supply at 38. The component is preferably an anesthetizing component, such as 1% lidocaine with epinephrine.

The cannula 34 may be a conventional design, as with a diameter of approximately 23 gauge.

The injection/guide unit 36 and tract forming unit 12 are preferably configured to be joinable from a separated state by advancing the cannula 34 into and through the through opening 27 from at the distal end 30 to place the same in operative relationship, as seen in FIGS. 1 and 2. The second dilating body section 22 and leading end 39 of the syringe 32 slide guidingly, one within the other, to operatively connect the injection/guide unit 36 and tract forming unit 12.

With the injection/guide unit 36 and tract forming unit 12 in their operative relationship, the tract forming unit 12 can be moved guidingly over and along the injection/guide unit 36 in the line of the double-headed arrow 40, generally parallel to the lengthwise/axial extent of the tract forming assembly 10. Through this relative movement, the injection/guide unit 36 and tract forming unit 12 can be selectively placed in: a) a first state, as shown in FIG. 1, wherein the cannula 34 projects a first length L3 beyond the cutting edge 14; and b) a second state, shown in FIG. 2, wherein the tract forming unit 12 is advanced axially/lengthwise relative to the cannula 34 in a direction as indicated by the arrow 42.

The tract forming unit 12 may be guided in lengthwise/axial movement against the syringe 32 and/or the cannula 34. The components may be guided closely against each other or, alternatively, there may be a relatively loose fit between the components.

In one form, the first section 20 has a diameter, on the order of 16 gauge, that is greater than the diameter of an IV catheter to be directed into the patient's vein. A typical IV catheter may have a diameter of 18-20 gauge.

The invention contemplates a method for preparing an access site, shown at 44 in FIGS. 6-8, for insertion of an IV catheter 46 into one of the patient's veins V using a tract forming assembly, such as the tract forming assembly 10, and variations thereof as contemplated and depicted generically in FIG. 9.

The inventive method in FIG. 10 involves the following steps. Initially, a tract forming assembly is provided, as shown at block 48. The tract forming assembly consists of at least a tract forming unit and more preferably an operatively connected tract forming unit and injection/guide unit.

As shown at block 50, the tract forming unit is advanced at the access site 44 to generate and dilate a tract.

As shown at block 52, once the dilated tract is formed, the tract forming unit is removed to allow a catheter to be directed through the pre-formed and empty tract and into the vein V.

The sequence of forming the tract through the patient's skin and subcutaneous tissue towards the vein V, using the exemplary, preferred form of tract forming assembly 10 described herein, is shown in FIGS. 6-8, wherein the tract forming unit 12 and injection/guide unit 36 are used together.

As shown in FIG. 6, the cannula 34 is advanced through the patient's skin S at the access site 44 and into the subcutaneous tissue ST. The syringe 32 can be operated in conventional fashion to inject the anesthetizing component 38 preparatory to advancing the tract forming unit 12 over and relative to the injection/guide unit 36. The cannula 34 has a projecting usable length that is selected to extend towards, into, or beyond the vein V. As depicted, the cannula 34 is directed into the vicinity of, but not into, the vein V. This initial step is carried out with the tract forming unit 12 and injection/guide unit 36 in the aforementioned first state, as shown in FIG. 1.

The tract forming unit 12 is then advanced over and relative to the cannula 34, as shown in FIG. 7, so that the first section 20 forms a tract T from the skin surface towards the vein V. The advancing cutting edge portions 15 cut into the skin and progressively form a tract T for the trailing and advancing dilating portion 17, which enlarges/dilates the tract T.

Once the dilated tract T is fully formed, the tract forming assembly 10 is fully separated, leaving the dilated tract unoccupied by any component, whereupon the IV catheter 46 can be inserted as shown in FIG. 7.

Preferably, the tract T, dilated with the first section 17 having a gauge on the order of 16, will be formed above the vein V to accept an 18-20 gauge IV catheter 46. The precise gauges of the first section 17 and catheter 46 are not critical. However, it is preferred that the first section 17 have at least a slightly greater diameter than that of the catheter 46. With the tract T pre-formed, there thus will be no substantial resistance from the skin and subcutaneous tissue to introduction of the IV catheter 46, which allows the provider to better sense the vein V as the IV catheter is inserted, even through thick, tawny skin and/or edematous subcutaneous tissues. Using the inventive concept, success rate of difficult IV starts may be increased, minimizing patient discomfort and lowering health care costs.

The precise construction of the tract forming assembly 10, as described herein, should not be viewed as limiting. The invention contemplates many variations thereof as shown within the broad schematic representation of a tract forming assembly at 10' in FIG. 9.

The tract forming assembly 10' consists of a tract forming unit 12' that is advanced preferably relative to guide structure, as shown at 54, which may be a syringe or other type of structure with or without the capability of injecting an anesthetizing component. This guide structure might be omitted. The components are preferably constructed so that they can be fully separated from the patient after the tract T is formed.

Another variation contemplated is one wherein the tract forming unit 12 and injection/guide unit 36 have a fixed relationship that is maintained as a tract is formed. The fixed relationship may be one as shown in FIG. 1 or 2 or another relationship.

Another variation contemplated is with respect to the cutting edge on the dilating body 16. In FIG. 11, a modified form of dilating body is shown at 16" and differs in that the cutting edge 14" thereon is formed to reside within a plane P that is at an angle to the lengthwise axis 18".

In FIG. 12, an optional cover is shown at 60 for a modified form of tract forming assembly at 10", incorporating the dilating body 16", together with the injection/guide unit 36 with the cannula 34. The cover 60 can be frictionally placed over the tract forming assembly 10" to shield the user from the projecting cannula 34. The cover 60 may have a shape generally conforming to the outer profile of the dilating body 16" and cannula 34 so as to allow it to be frictionally engaged therewith to be releasably held in place. The cover 60 could be used in like fashion with the tract forming assembly 10.

In FIG. 13, an optional cover assembly 62 is shown operatively associated with the tract forming assembly 10"'. The cover assembly 62 consists of a sleeve 64 that surrounds and is connected to the syringe 32 on the injection/guide unit 36 and operatively positioned tract forming unit 12". The sleeve 64 is movable relative thereto between the solid and dotted line position shown in FIG. 13, with the former representing a covering state for the cover assembly 62 and the latter representing an operative state for the cover assembly 62. The sleeve 64 may be connected to the tract forming unit 12" and/or the injection/guide unit 36 for guided movement between the solid and dotted line positions in FIG. 13. Diametrically oppositely projecting tabs 70, 72 facilitate manipulation of the sleeve 64 through the user's fingers.

The foregoing disclosure of specific embodiments is intended to be illustrative of the broad concepts comprehended by the invention.

The invention claimed is:

1. A method for preparing an access site on a patient for insertion of a catheter into one of the patient's veins, the method comprising the steps of:
   providing a tract forming assembly comprising a leading cutting edge and a dilating body defining a trailing dilating portion, the cutting edge and dilating body together defining a tract forming unit;
   advancing the tract forming unit into skin at the access site so that: a) the cutting edge progressively forms a tract through the patient's skin and subcutaneous tissue towards the one vein; and b) the dilating body follows the cutting edge and dilates the tract;
   removing the tract forming unit from the dilated tract so that the dilated tract is empty; and
   directing a catheter through the dilated and empty tract and into the one vein after the tract forming unit is removed.

2. The method for preparing an access site for insertion of a catheter according to claim 1 wherein the step of advancing the tract forming unit comprises advancing the tract forming unit so that the cutting edge forms a tract fully up to the one vein.

3. The method for preparing an access site for insertion of a catheter according to claim 2 wherein the step of advancing the tract forming unit comprises advancing the tract forming unit so that the dilating body dilates the tract fully up to the one vein.

4. The method for preparing an access site for insertion of a catheter according to claim 1 wherein the step of providing a tract forming assembly comprises providing a tract forming assembly wherein the cutting edge moves as one piece with the dilating body.

5. The method for preparing an access site for insertion of a catheter according to claim 1 wherein the step of providing a tract forming assembly comprises providing a tract forming assembly wherein the cutting edge is formed on the dilating body.

6. The method for preparing an access site for insertion of a catheter according to claim 1 wherein the step of providing a tract forming assembly comprises providing a tract forming assembly wherein the dilating body has an axis and leading and trailing ends spaced lengthwise of the dilating body along the axis, and the dilating body comprises a first section with a first axial length with one of: a) a substantially constant diameter; and b) a diameter that increases axially from the leading end towards the trailing end of the dilating body.

7. The method for preparing an access site for insertion of a catheter according to claim 6 wherein the step of providing a tract forming assembly comprises providing a tract forming assembly wherein the dilating body comprises a second section with a diameter greater than an average diameter of the first section and a transition region between the first and second sections.

8. The method for preparing an access site for insertion of a catheter according to claim 7 wherein the step of providing a tract forming assembly comprises providing a tract forming assembly wherein the first and second sections and transition region are formed as one piece.

9. The method for preparing an access site for insertion of a catheter according to claim 7 wherein the step of providing a tract forming assembly comprises providing a tract forming assembly wherein the first section has at least a portion with a diameter on the order of 16 gauge.

10. The method for preparing an access site for insertion of a catheter according to claim 1 wherein the step of providing a tract forming assembly comprises providing a tract forming assembly that additionally comprises a cannula with a length and further comprising the step of advancing the cannula through the patient's skin at the access site and the step of advancing the tract forming unit comprises advancing the tract forming unit one of: a) lengthwise along the cannula after the cannula is advanced through the patient's skin; and b) together with the cannula with the tract forming unit and cannula in fixed relationship.

11. The method for preparing an access site for insertion of a catheter according to claim 10 wherein the step of providing a tract forming assembly comprises providing a tract forming assembly that additionally comprises a syringe with an anesthetizing component and further comprising the step of injecting the anesthetizing component in the syringe through the cannula and into the patient at the access site before advancing the tract forming unit into the patient's skin.

12. The method for preparing an access site for insertion of a catheter according to claim 11 wherein the step of providing a tract forming assembly comprises providing a tract forming assembly wherein the cannula extends into and from the tract forming unit and the step of advancing the tract forming unit comprises advancing the tract forming unit guidingly over and relative to the cannula.

13. The method for preparing an access site for insertion of a catheter according to claim 11 wherein the step of providing a tract forming assembly comprises providing a tract forming assembly wherein a portion of the syringe is inserted into the tract forming unit.

14. The method for preparing an access site for insertion of a catheter according to claim 12 wherein the step of providing a tract forming assembly comprises providing a tract forming assembly wherein the tract forming unit has an axis and the cutting edge at least one of: a) resides in a plane that is at an angle to the axis; and b) has a plurality of discrete cutting edge portions.

15. The method for preparing an access site for insertion of a catheter according to claim 1 wherein the step of providing a tract forming assembly comprises providing a tract forming assembly wherein the dilating body has an axis and a length along the axis between leading and trailing ends, the tract forming assembly further comprising a syringe with a cannula together defining an injection/guide unit, the cutting edge and dilating body movable together as one piece, the dilating body comprising a first section with a length between the cutting edge and the trailing end of the dilating body, the first section having at least a portion with one of: a) a substantially constant diameter; and b) a diameter that increases axially from the leading end towards the trialing end of the dilating body.

16. The method for preparing an access site for insertion of a catheter according to claim 15 wherein the step of providing a tract forming assembly comprises providing a tract forming assembly wherein the tract forming unit and injection/guide unit are configured to cooperate so that: a) with the tract forming unit and injection/guide unit in a first state the cannula projects from the tract forming unit and can be advanced through a patient's skin at an access site towards a vein; and b) with the tract forming unit and injection/guide unit in the first state and the cannula advanced through a patient's skin the tract forming unit can be advanced guidingly over and relative to the cannula to cause the tract forming unit and injection/guide unit to be changed to a second state, as an incident of which a tract is cut at the access site and thereafter dilated.

17. The method for preparing an access site for insertion of a catheter according to claim 16 wherein the step of providing a tract forming assembly comprises providing a tract forming assembly wherein the cutting edge is formed on the dilating body and the dilating body comprises a second section with a length and a diameter greater than an average diameter of the first section and there is a transition region between the first and second sections and the first and second sections, transition region, and cutting edge are formed as one piece.

18. The method for preparing an access site for insertion of a catheter according to claim 16 wherein the step of providing a tract forming assembly comprises providing a tract forming assembly wherein the first section has at least a portion with a diameter on the order of 16 gauge.

19. The method for preparing an access site for insertion of a catheter according to claim 16 wherein the step of providing a tract forming assembly comprises providing a tract forming assembly wherein the tract forming unit has a through opening and the injection/guide unit extends into and through the through opening.

20. The method for preparing an access site for insertion of a catheter according to claim 16 wherein the step of providing a tract forming assembly comprises providing a tract forming assembly wherein the syringe contains a supply of an anesthetizing component that can be injected at the access site.

21. The method for preparing an access site for insertion of a catheter according to claim 16 wherein the step of providing a tract forming assembly comprises providing a tract forming assembly wherein the cutting edge at least one of: a) resides in a plane that is at an angle to the axis of the tract forming unit; and b) has a plurality of discrete cutting edge portions.

22. The method for preparing an access site for insertion of a catheter according to claim 18 in combination with a catheter having a diameter less than the diameter of the portion of the first section.

23. The method for preparing an access site for insertion of a catheter according to claim 16 wherein the step of providing a tract forming assembly comprises providing a tract forming assembly wherein the tract forming assembly further comprises a cover assembly that can be changed between: a) an operative state wherein the cutting edge and/or the cannula is exposed; and b) a covering state.

24. The method for preparing an access site for insertion of a catheter according to claim 23 wherein the step of providing a tract forming assembly comprises providing a tract forming assembly wherein the cover assembly is connected to at least one of the tract forming and injection/guide units with the cover assembly in both the operative and covering states.

* * * * *